United States Patent [19]

Sullivan et al.

[11] Patent Number: 4,720,458

[45] Date of Patent: Jan. 19, 1988

[54] HEAT SENSITIVE BACTERIAL ALKALINE PHOSPHATASE

[76] Inventors: Cornelius W. Sullivan, 5629 Marialinda St., Torrance, Calif. 90503; Hiroaki Shizuya, 1632 Indiana Ave., South Pasadena, Calif. 91030; Hiromi Kobori, 1-8, Toyotama, Kita, Nerima-ku, Tokyo, Japan

[21] Appl. No.: 543,435

[22] Filed: Oct. 19, 1983

[51] Int. Cl.$^4$ .................... C12N 9/16; C12Q 1/42; C12Q 1/68
[52] U.S. Cl. ..................... 435/196; 435/21; 435/6
[58] Field of Search ................ 435/196, 21

[56] References Cited

PUBLICATIONS

Glen et al, Journal of Biological Chemistry, vol. 246, pp. 1556–1565 (1974).
Advances in Enzymology, vol. 55, pp. 381–386 (1983).

*Primary Examiner*—Lionel M. Shapiro
*Attorney, Agent, or Firm*—Blakely, Sokoloff, Taylor & Zafman

[57] ABSTRACT

This invention discloses a newly discovered enzyme and a method of producing said enzyme wherein said enzyme is completely inactivated by treatment with temperatures of 50° or higher for 10 minutes or longer. The alkaline phosphatase is isolated from the psychrophilic bacteria, particularly bacteria from certain areas of the oceans surrounding Antarctica. The preferred alkaline phosphatase is derived from the bacteria HK-47 (ATCC 39469).

2 Claims, 9 Drawing Figures

HEAT SENSITIVE BACTERIAL ALKALINE PHOSPHATASE

FIELD OF THE INVENTION

The present invention relates to the field of nucleic acid research, and more particularly to an enzyme useful in performing radioactive end-labeling of nucleic acids.

BACKGROUND OF THE INVENTION

Alkaline phosphatase (APase) is an enzyme which catalyzes the hydrolysis of an ester bond of terminal phosphate groups ($PO_4^-$). This reaction is useful as a research tool particularly for radioactive end-labeling of nucleic acids using T4 polynucleotide kinase to study nucleic acid structure and function.

In the procedure for radioactive end-labeling, the substrate, such as DNA, RNA or an oligonucleotide, is first dephosphorylated with APase prior to the labeling step. In the next step, the APase activity must then be eliminated to avoid both degradation of ATP and loss of label from the nucleotide substrates. Finally, polynucleotide kinase (PNK) is used to catalyze the phosphorylation of the substrate, wherein the phosphate donor is typically a gamma-$P^{32}$ATP. As noted above, residual APase activity in the reaction vessel during or subsequent to the phosphorylation step, can result in a loss of label from the ATP and polynucleotide substrate, thereby destroying the results of the radioactive end-labeling reaction.

Most researchers are using APase isolated from the microorganism *E. coli*, which is available commercially, to cleave the terminal phosphates from the nucleotide substrate. The disadvantage of this enzyme is its great stability, especially its heat stability, which makes inactivation of the APase particularly difficult.

Severaly methods are currently employed to remove or inactivate *E. coli* APase from the phosphorylation reaction vessel prior to the labeling step. The most effective method is phenol extraction; however, this method is time-consuming, results in poor recovery of nucleic acids and is inappropriate for processing large numbers of samples. Methods of treatment with NaOH, HCl, boiling, or nitriliatriacetic acid are not suitable because the APase is not completely inactivated thereby. One other method is the use of inorganic phosphate (Pi) to inhibit APase activity. This method is disadvantageous in that Pi also inhibits polynucleotide kinase activity, so that the phosphate labeling of highly structured polynucleotide substrate, such as DNA or RNA, is also greatly reduced. The general problem with the above methods is that *E. coli* APase is highly stable making removal or inactivation thereof difficult.

One solution to the above-noted problems of the stability of *E. coli* APase in end-labeling experiments is to use heat sensitive APase. Some heat sensitive APases are disclosed in *Alkaline Phosphatase*, R. B. McComb, et. al. (1979), Plenum Press, N.Y. p. 404 in "Table of Thermal Denaturation Rates of Selected Microbial Alkaline Phosphatases." As stated therein, the APases which are most heat sensitive include *Bacillus megaterium* with a half-life of 4 minutes at 55° C., and Sacharomyces cerevisiae with a half-life of 2.5 minutes at 60° C. However, the report of these temperature sensitive APases does not disclose what treatment is necessary for complete APase inactivation, and there is no necessarily direct relationship between half-life (50% inactivation of enzyme activity) and complete inactivation of the enzyme. Moreover, effective phosphorylation of the polynucleotide substrate can only occur if the APase is completely inactivated.

One particularly significant problem with using temperature treatment to inactivate APase is that double stranded polynucleotides are somewhat heat labile. This problem is caused by the fact that double stranded DNA, RNA and oligonucleotides are held together by hydrogen bonding which can be broken at elevated temperatures. Shorter polynucleotide double stranded chains and those polynucleotides containing a large percentage of adenine-thymine base pairs are examples of particularly temperature sensitive polynucleotides. In fact, double stranded DNA can be completely denatured by heat treatment at 65° C. Thus, it is preferable for radioactive end-labeling procedures, where the integrity of the polynucleotide substrate may be important that the temperature of heat treatment of the polynucleotide substrate be as low as possible, and the duration of such treatment be short. The present invention obviates the need for higher elevated temperatures or other extreme conditions for removing or inactivating APase.

SUMMARY OF THE INVENTION

The present invention comprises a new form of the enzyme alkaline phosphatase, isolated from microorganisms collected from Antarctica. These microorganisms were collected from a number of sources such as the sea ice, sea water and sediment around the McMurdo Sound in Antarctica. Twenty-two of the 150 strains of bacteria tested produced heat sensitive alkaline phosphatase which was completely inactivated by heat treatment at 65° C. for 10 minutes. The alkaline phosphatase from one strain, HK-47 (ATCC 39469), which has a maximum growing temperature of less than 25° C., showed the highest activity among the heat sensitive APase producers. It was determined that this strain produced an APase which was inactivated substantially instantaneously at 50° C. The half-life at 40° C. was determined to be 2.0 minutes.

The advantage to this invention over the prior art is that the alkaline phosphatase disclosed herein may be inactivated completely by a simple, safe and quick procedure. In the case of end-labeling experiments, nucleotides may be dephosphorylated using the alkaline phosphatase disclosed herein. The reaction vessel is then heat treated at 50° C. for 10 minutes to completely inactivate the APase. Polynucleotide Kinase and radioactive Adenosine Triphosphate (gamma-$^{32}p$-ATP) may then be added directly to the original reaction vessel, thereby labeling the dephosphorylated nucleotide, and thus avoiding the inconvenience and potential loss of yields through multiple transfers of the reaction mixture. Temperature treatment of nucleic acids at 50° C. for 10 minutes which is more than sufficient to inactivate the invented APase, and does not generally permit denaturation of RNA, DNA or oligonucleotide substrates on which the end-labeling is performed.

Whereas 21 strains of bacteria have been found to produce heat sensitive enzymes of alkaline phosphatase, it is anticipated that other strains of bacteria, yet undiscovered but existing under similar environmental conditions, will be found to be useful in practicing the present invention without departing from the scope thereof.

DETAILED DESCRIPTION OF THE SPECIFIC EMBODIMENT

Figure 1:
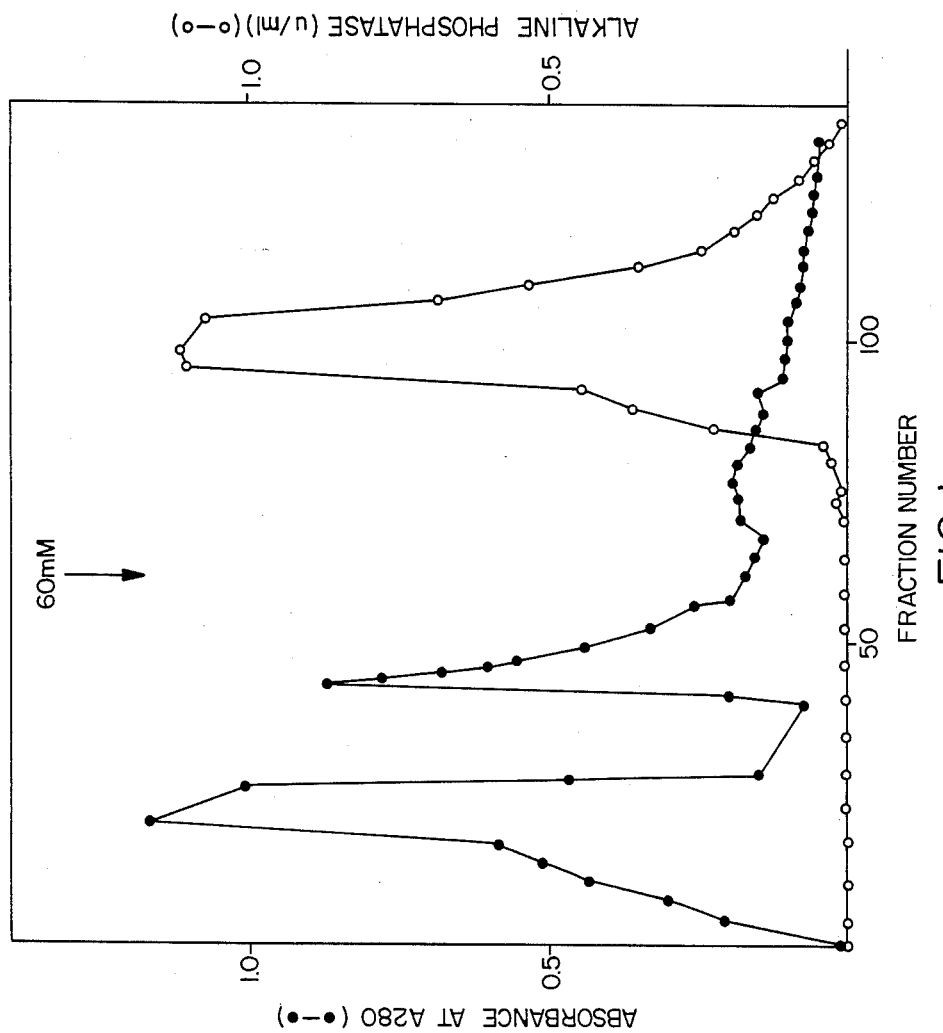
FIG. 1 is a graph of the affinity column chromatography of osmotic shock fluid.

1. Isolation of Antarctic Bacteria and Screening of Heat Labile APase

It is generally agreed that psychrophilic bacteria are found in permanently cold environments. Most of the well characterized psychrophilic bacteria were isolated from the ocean. Since more than 90% of the ocean is at a temperature of 5° C. or below, the ocean is a natural habitat for psychrophilic bacteria. It is expected that psychrophilic bacteria can be isolated relatively easily below the thermocline of the ocean, particularly from polar regions. For this reason, we decided to isolate psychrophilic bacteria from the antarctic.

Various samples of sea ice, sea water, sea sediments, and sea animals were obtained from two areas of Antarctica (McMurdo Sound and New Harbour). The frozen samples of seawater and sea ice were melted at 0° C. and 0.1 ml of serially diluted samples was spread onto agar plates containing 2216E medium. Animal samples were homogenized before spreading onto the plates for bacterial colonies.

One hundred and sixty-six colonies appeared after two to twelve weeks incubation at 0° C. Among these 41 strains (24%) were found to be psychrophiles. Twenty-two strains (including 3 psychrophiles) produced heat labile APase which is completely inactivated after incubating at 65° C. for 10 minutes. The APase from strain HK-47 yielded the highest activity among the 22 heat labile APase producers. HK-47 showed the maximum growth rate in medium containing 60% sea water and no growth over three days in media containing no seawater. HK-47 is a psychrophilic bacterium having an optimal growth temperature of about 15° C., a maximal growth temperature of 22°-24° C., and a minimal growth temperature of 0° C. or lower. The HK-47 strain is on deposit with the ATCC (No. 39469). Pursuant to the applicant's contract with the ATCC, the micro-organism identified as HK-47, shall be maintained on deposit for at least 30 years and will be available to the public, without restriction, after the patent issued for at least as long as the life of the patent.

2. Purification and Characterization of HK-47 APase

All purification procedures were carried out at 0°-4° C. Marine bacteria HK-47 was grown at 0°-4° C. in HK medium, containing 60% aged seawater, 1% Bactotryptone, and 0.2% yeast extract. The medium was buffered at pH 7.6 with HCl before inoculation of the bacteria. The cells grown to late exponential phase in 5.4 liters were harvested by centrifugation at 10,000 xg for 15 minutes at 0° C.

APase activity appears to be localized in the periplasmic space outside the cytoplasmic membrane of all gram-negative bacteria. Therefore, the first step in the purification procedure is to treat cells by osmotic shock. Sixty percent (60%) of the total APase is successfully released by a modified osmotic shock procedure as described by Unemoto, (1973 Biochem. Biophys. Acta, 315, 83–93), whereas only 6% of the total protein was solubilized from HK-47 cells under the same conditions.

The harvested cells were washed by centrifugation in 5.4 liters of 1M NaCl in 50 mM Tris-HCl buffer, pH 7.4, suspended in 350 ml of hypertonic medium containing 1.0M NaCl, 1.0M sucrose, and 50 mM Tris-HCl buffer pH 7.4, and then stirred for 15 min at 0° C. The cell suspension was centrifuged and the pellet was rapidly suspended in 54 ml of cold shock buffer containing 50 mM NaCl, 10 mM $MgCl_2$, and 50 mM Tris-HCl pH 8.0. After stirring for 15 min at 0° C., the mixture was centrifuged and the supernatant was collected. The pellet was further extracted with 27 ml of the shock buffer, and two supernatants were combined. The osmotic shock fluid was dialyzed against 50 mM Tris-HCl buffer pH 8.4 containing 5 mM NaCl, and 10% glycerol (T buffer) and centrigued at 100,000 xg for 30 minutes.

The supernatant was applied to affinity chromatograph column (0.8 $cm^2 \times 12$ cm) equilibrated with 10 mM Tris-HCl buffer pH 8.4. The affinity chromatography was prepared by coupling diazonium salt of 4-(p-aminophenylazo) phenyl arsenic acid to a tryaminyl-Sepharose as described by Brenna et al. (1975 Biochem. J., Vol. 151, p. 291). The column was washed with, first, 5 mM NaCl in 10 mM Tris-HCl pH 8.5, and then 5 mM NaCl in 100 mM Tris-HCl buffer pH 8.4. The APase was eluted by a linear gradient from 20 to 100 mM sodium phosphate in 150 mM Tris-HCl buffer pH 8.4, and 5 mM NaCl (FIG. 1). The APase peak fraction was pooled and dialyzed against T buffer.

The dialyzate was applied on DEAE-Sephacel column (0.5 $cm^2 \times 10$ cm) equalibrated with T buffer, and the APase was eluted by a linear gradient from 0 to 0.4 m NaCl in T buffer. (FIG. 2) The pooled fraction of the enzyme was dialyzed against, first, T buffer and second, 50% glycerol in 10 mM Tris, pH 8.4. The purified enzyme was stored at $-20°$ C.

A summary of purification scheme is presented in Table 1 (below).

TABLE 1

| Summary of purification scheme for HK-47 APase. | | | | |
|---|---|---|---|---|
| Purification step | Total protein mg | Total units U | Specific activity U/mg protein | Total recovery % |
| Osmotic shock fluid | 110.0 | 668.5 | 5.8 | 100 |
| Affinity chromatography | 4.5 | 138.7 | 30.8 | 21 |
| DEAE-Sephacel | 0.08 | 72.5 | 906.3 | 11 |

Figure 2:
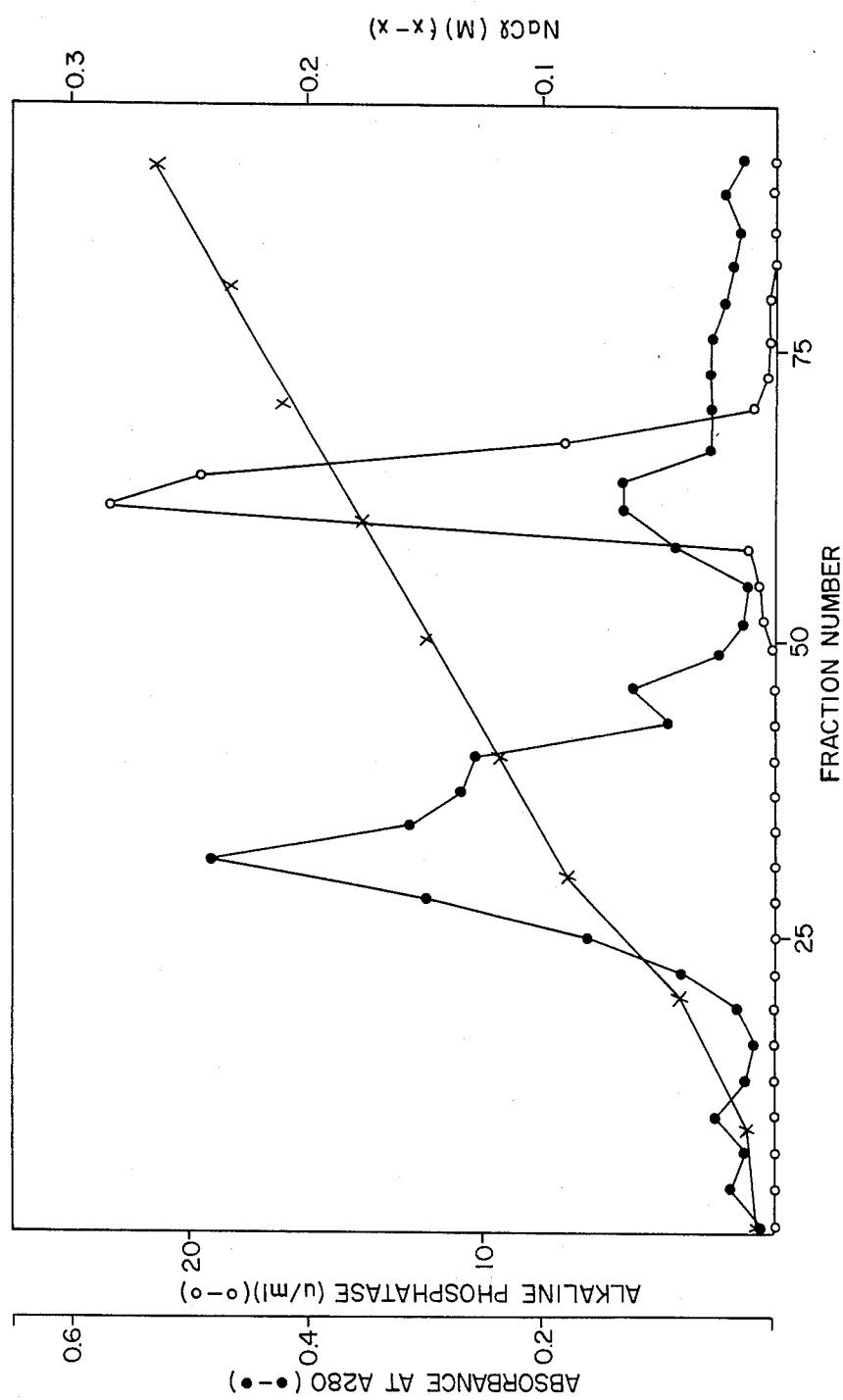
FIG. 2 is a graph of the DEAE-Sephacel chromatography of the pooled fraction from the affinity chromatography column.

More than 90% of the total proteins in the osmotic shock extract were not absorbed by the affinity column, and APase activity was eluted at approximately 60 mM sodium phosphate (FIG. 1). As shown in FIG. 2, APase of the pooled fraction from the affinity column appeared at 190 mM as a single peak on DEAE Sephacel column. In separate experiments, when osmotic shock extract was directly applied onto DEAE Sephacel column, APase activity was found in two peaks.

The pooled fraction of DEAE Sephacel chromatography was analyzed by SDS gel electrophoresis. One major band (69,000) and three minor bands were seen after silver staining. The molecular weight of the native enzyme was found to be 67,000 by P200 gel filtration, indicating that native HK-47 APase is uniquely monomeric. The specific activity of the APase obtained after DEAE Sephacel is among the highest so far reported for the bacterial APases. Although the final specific activity varied from one experiment to another, a specific activity of 800–1,600 units per mg protein were generally obtained.

The HK-47 APase does not require the four major cations in seawater ($Na^+$, $K^+$, $Ca^{2+}$, and $Mg^{2+}$) for the manifestation of its activity, although $Ca^{2+}$ is required for maximum activity. In the presence of 10 mM $Ca^{2+}$, the activity of HK-47 APase was 6 times higher than the activity seen without adding any cations in the assay mixture.

HK-47 APase activity was inhibited 50% by as little as 0.1 mM EDTA and almost 100% at 1 mM EDTA. In contrast, 50% of the inactivation of *E. coli* APase occurs at 10 mM, so that HK-47 APase is 100-fold more sensitive to EDTA. HK-47 APase is also more sensitive to lower pH, activity thereof being lost irreversibly when said APase is treated at pH 4.5 for 10 min at 4° C.

Figure 3B:
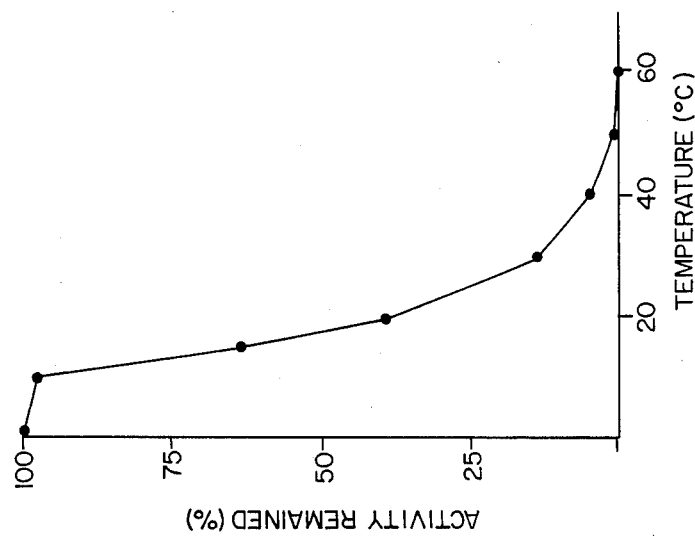
FIG. 3b is a heat inactivation curve of HK-47 APase activity.
Figure 3A:
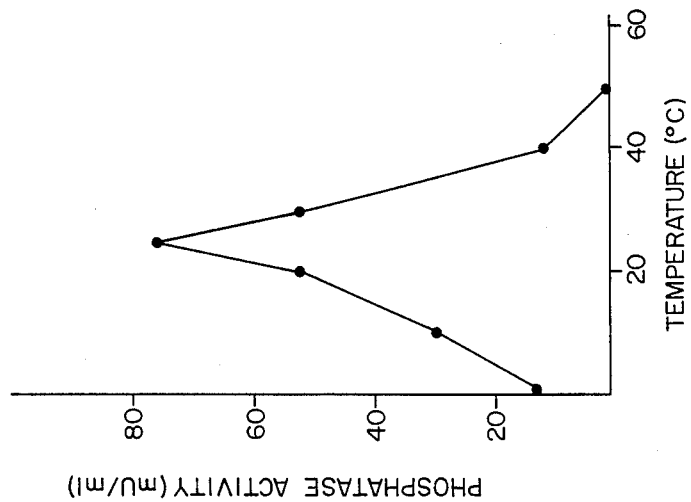
FIG. 3a is a graph of reaction temperature versus HK-47 APase activity.

The enzymatic activity of HK-47 phosphatase is particularly sensitive to temperature. The optimum temperature for the activity is 25° C. (FIG. 3a). The enzyme is still active at 0° C. and 17% of the maximum activity was seen at this temperature. As the assay temperature was raised, the APase activity rapidly decreased, and at 50° C. virtually no activity was detected.

Further, the APase is rapidly inactivated during incubation at higher temperature. HK-47 APase was incubated for 10 minutes in 50 mM Tris-HCl buffer at the temperatures indicated in FIG. 3b. Little loss of the activity was seen at 10° C. incubation. However, even at 15° C., 40% of the activity was lost during the incubation. Very little activity remained above 50° C. incubation.

Figure 4A:
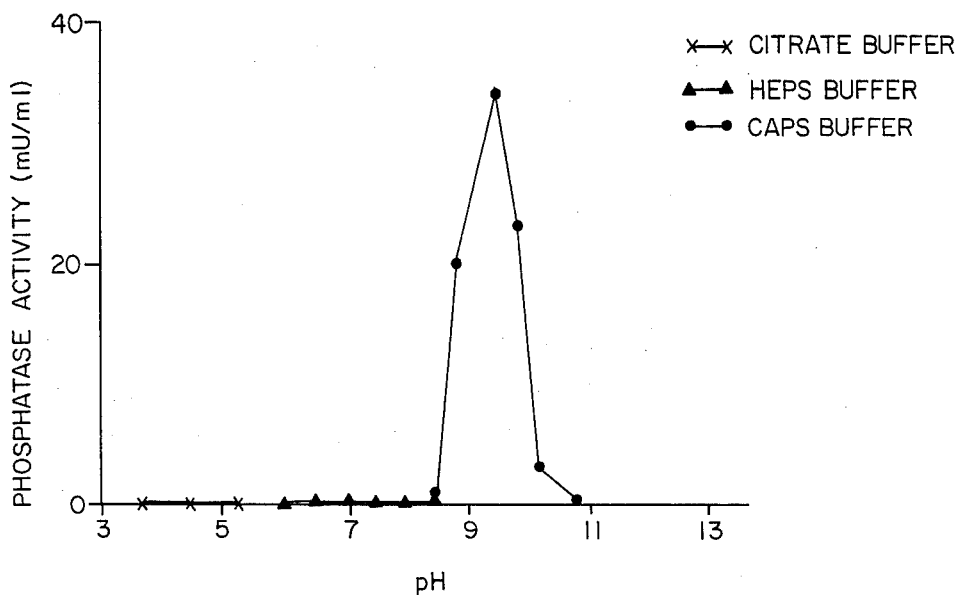
FIG. 4a is a graph showing optimum pH of HK-47 APase activity.
Figure 4B:
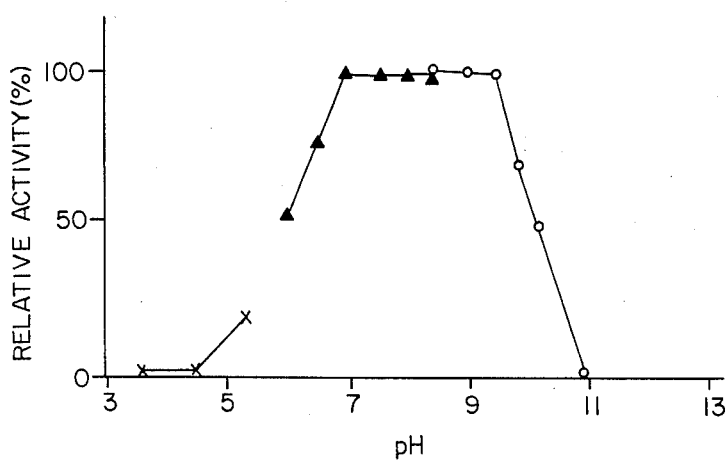
FIG. 4b is a graph showing the stability of HK-47 APase at indicated pH.

The enzyme was found to be stable within a range of pH 7.0 to 9.5 when it was incubated at 0° C. for 10 minutes at such pH (FIG. 4b). However, the enzyme was active only at pH 8.5 to pH 10.0; and its maximum enzyme activity was found at pH 9.5 (FIG. 4a.) The half-life time of HK-47 APase was 40° C. at 2 min. Thermal inactivation of the APase was detectable even at 15° C. and the APase was completely inactivated by heat treatment of 50° C. for 10 minutes.

3. Analysis of Enzyme Activity

Figure 5B:
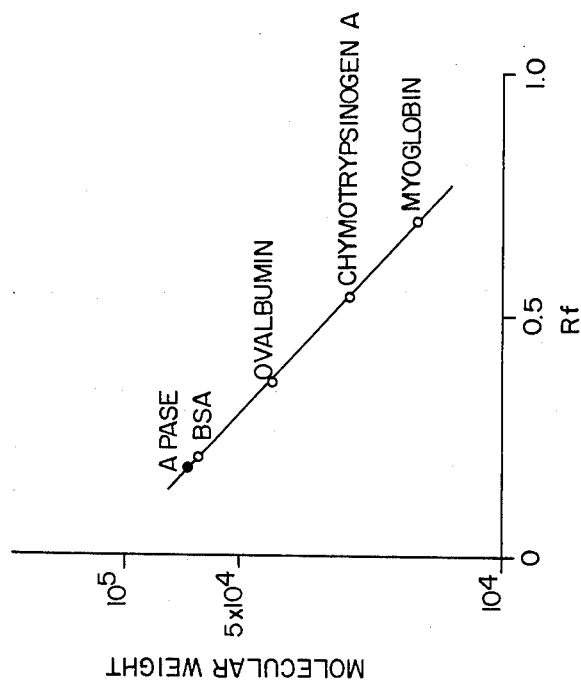
FIG. 5b is a graph of molecular weight determination of HK-47 APase by SDS gel electrophosesis.
Figure 5A:
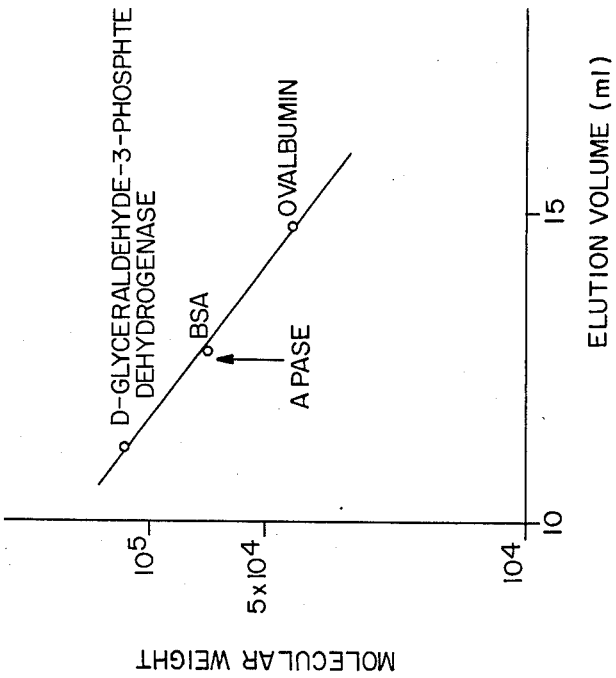
FIG. 5a is a graph of molecular weight determination of HK-47 APase by Bio-gel P200 gell filtration.

APase activity was routinely assayed at 25° C. for 30 min in 100 μl reaction mixture containing 2 mM p-nitrophenyl phosphate, 5 mM $CaCl_2$, 0.1M CAPS-NaOH buffer pH 9.5. The reaction was stopped by adding 300 μl of 13% (W/V) EDTA-1N NaOH to the reaction mixture. Control mixtures were similarly prepared, except that 13% EDTA-1N NaOH was added before the enzyme activity was assayed. APase activity was measured as the difference in absorbance at 410 nm between samples and control. One unit of APase activity is expressed as 1 micromole of p-nitrophenol (pNp) liberated per minute at 25° C. under the assay conditions. Protein concentration was determined by the Bio-Rad protein assay kit. Bovine serum albumin (BSA) was used as the standard. Homogeneity of the APase was examined by polyacrylamide gel electrophoresis and Bio-Rad (Bio-Rad laboratories, Richmond, CA.) silver stain. Molecular weight was determined by Biogel P200 gel filtration (FIG. 5a) and SDS gel electrophorosis (FIG. 5b) to be approximately 67,000 daltons.

4. Radioactive End-Labeling Using HK-47 APase

Figure 6:
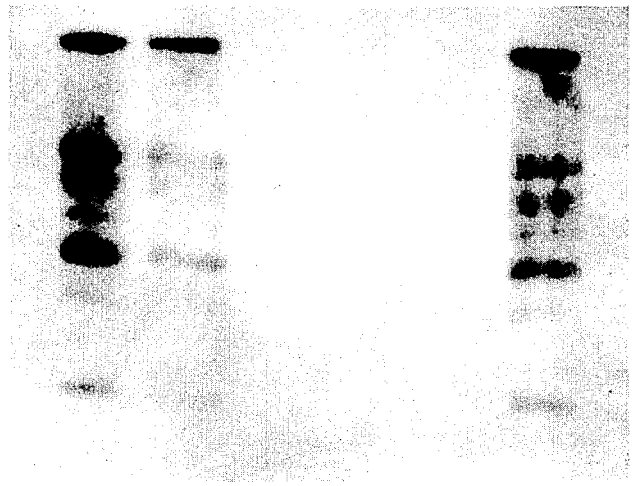
FIG. 6 is an illustration of an autoradiograph of Hinf-I DNA fragments treated under various conditions.

An autoradiograph of the end-labeled Hinf-I DNA fragments with serial treatments of HK-47 APase and polynucleotide Kinase is illustrated in FIG. 6. Five micrograms of pBR322 DNA were digested by 250 units of Hinf-I restriction enzyme in 100 μl reaction mixture of 10 mM Tris-HCl, pH 7.5, 50 mM NaCl, 10 mM $MgCl_2$, 1 mM beta-mercaptoethanol, and 15 micrograms of BSA at 37° C. for 16 hr. The terminal phosphate groups of the Hinf-I treated DNA fragments were removed by either HK-47 or *E. coli* APase. Using HK-47 APase, 0.2 micrograms of Hinf-I fragments were incubated in 10 μl of 100 mM CAPS-NaOH pH 9.5, 5 mM $CaCl_2$, and 0.04 units of HK-47 APase at 25° C. for 1 hr. Another sample of a 0.2 micrograms of Hinf I fragments were also dephosphorylated in 10 μl of 100 mM Tris-HCl pH 8.0, and 0.04μ of *E. coli* APase at 37° C. for 1 hr. Both reaction mixtures were incubated at 60° C. for 10 minutes, and then brought to 0° C. Phosphorlyation was carried out by adding 10 microliters of a mixture containing 25 mM Hepes-NaOH, pH 7.5, 10 mM dithiothreitol, 10 mM $MgCl_2$, 0.36 micromoles of [gamma-$^{32}p$] ATP (3,000 Ci/mmole), and 1.6 units of polynucleotide kinase. Reaction mixtures were incubated at 37° C. for 30 min, and then chilled on ice. One microliter of the kinase reaction mixture was mixed with 4 microliters of dye solution containing 0.05% xylene cyanol. 0.05% bromophenol blue (BPB), and 8.3M urea in TBE buffer (2.5 mM EDTA, 39 mM boric acid, and 89 mM Trizma base). Samples were loaded onto 10% polyacrylamide slab gel and electrophoresed in TBE buffer at 400 volts until the BPB dye reached to 12 cm from the top of the gel. The $^{32}p$-DNA fragments were visualized by exposing the gel to Kodak XAR-5 ray film for 90 min at −70° C. (FIG. 6). Lanes 1 and 6 contain $^{32}p$-labeled pBR322 Hinf-I fragment controls treated with *E. coli* bacterial alkaline phosphatase (BAP) was inactivated using a phenol extraction technique well known in the art. Lanes 2 and 4 contain 32p-labelled pBR322 Hinf-I fragments treated with HK-47 and *E. coli* APase, respectively, and heat treated at 60° C. as described above. Lanes 3 and 5 contain 32pBR322 Hinf-I fragments treated wtih HK-47 and *E. coli* Apase, respectively, and kept at 0° C. for 10 minutes, rather than receiving heat treatment.

We claim:

1. The process for producing alkaline phosphatase having the characteristic of being inactivated by heating to a temperature of at least 50° C. for at least 10 minutes comprising the steps of:

isolating the microorganism HK-47 (ATCC 39469);
   cultivating said microorganism in an aqueous solution containing assimilable quantities of carbon, nitrogen and oxygen; and
   purifying the enzyme alkaline phosphatase from said culture of microorganisms.

2. The process of claim 1 wherein said purification step comprises the steps of:

osmotically shocking said culture to release protein contained in said microorganisms therefrom;

concentrating the released protein using ammonium sulfate fractionation;

purifying the concentrated protein fraction by column chromatography;

separating said alkaline phosphatase from said concentrated protein using gel filtration chromatography.

* * * * *